United States Patent
Becker et al.

(10) Patent No.: US 6,904,161 B1
(45) Date of Patent: Jun. 7, 2005

(54) WORKFLOW CONFIGURATION AND EXECUTION IN MEDICAL IMAGING

(75) Inventors: Douglas E. Becker, South Elgin, IL (US); Sreenivasan Narayanan, Arlington Heights, IL (US); Govind Pai, Aurora, IL (US); Robert W. Mackin, Jr., Streamwood, IL (US); Keith M. Andress, Barrington, IL (US); William B. Pratt, Bartlet, IL (US); Kevin P. O'Donnell, Pacifica, CA (US); Kris Durski, Castro Valley, CA (US); Atsushi Habara, Otawara (JP); Takashi Tanaka, Otawara (JP); Susumu Matsui, Otawara (JP)

(73) Assignee: Siemens Medical Solutions USA, Malvern, PA (US)

( * ) Notice: Subject to any disclaimer, the term of this patent is extended or adjusted under 35 U.S.C. 154(b) by 497 days.

(21) Appl. No.: 09/714,877

(22) Filed: Nov. 17, 2000

(51) Int. Cl.[7] ................................................ G06K 9/00
(52) U.S. Cl. ...................................... 382/128; 700/15
(58) Field of Search ........................... 382/128; 700/11, 700/15; 707/1, 100, 200; 600/437

(56) References Cited

U.S. PATENT DOCUMENTS

| | | | |
|---|---|---|---|
| 4,835,690 A | 5/1989 | Gangarosa et al. | 364/413.13 |
| 5,247,661 A | 9/1993 | Hager et al. | 395/600 |
| 5,319,543 A | 6/1994 | Wilhelm | 364/401 |
| 5,321,520 A | 6/1994 | Inga et al. | 358/403 |
| 5,655,084 A | 8/1997 | Pinsky et al. | 395/203 |
| 5,715,823 A | 2/1998 | Wood et al. | 128/660.01 |
| 5,740,428 A | 4/1998 | Mortimore et al. | 395/615 |
| 5,745,901 A | 4/1998 | Entner et al. | 707/103 |
| 6,038,541 A | 3/2000 | Tokuda et al. | 705/8 |
| 6,041,306 A | 3/2000 | Du et al. | 705/8 |
| 6,047,081 A | 4/2000 | Groezinger et al. | 382/128 |
| 6,101,407 A | 8/2000 | Groezinger | 600/407 |
| 6,458,081 B1 * | 10/2002 | Matsui et al. | 600/437 |
| 6,574,629 B1 * | 6/2003 | Cooke, Jr. et al. | 707/10 |
| 6,603,494 B1 * | 8/2003 | Banks et al. | 345/807 |

FOREIGN PATENT DOCUMENTS

| | | |
|---|---|---|
| DE | 199 04 090 A1 | 8/2000 |
| EP | 0 473 414 A2 | 3/1992 |
| EP | 0 831 406 A2 | 3/1998 |
| WO | WO 97/15022 A1 | 4/1997 |
| WO | WO 97/32271 | 9/1997 |
| WO | WO 99/44166 A1 | 9/1999 |

OTHER PUBLICATIONS

Wong, S.T.C., et al., IEEE Transactions on Systems, Man & Cybernetics, Part A (Systems & Humans), Jul. 1996, IEEE, USA, vol. 26, No. 4, pp. 455–469, XP000593210.

* cited by examiner

*Primary Examiner*—Leo Boudreau
*Assistant Examiner*—Ryan J. Miller

(57) ABSTRACT

A computer-implemented method and apparatus is provided for workflow configuration and execution in medical imaging. One method embodiment comprises the steps of creating and storing a workflow template (the workflow template comprising a standard form for entering data and activities), filling out the workflow template with data and a sequence of activities, and executing the sequence of activities according to the workflow template.

20 Claims, 8 Drawing Sheets

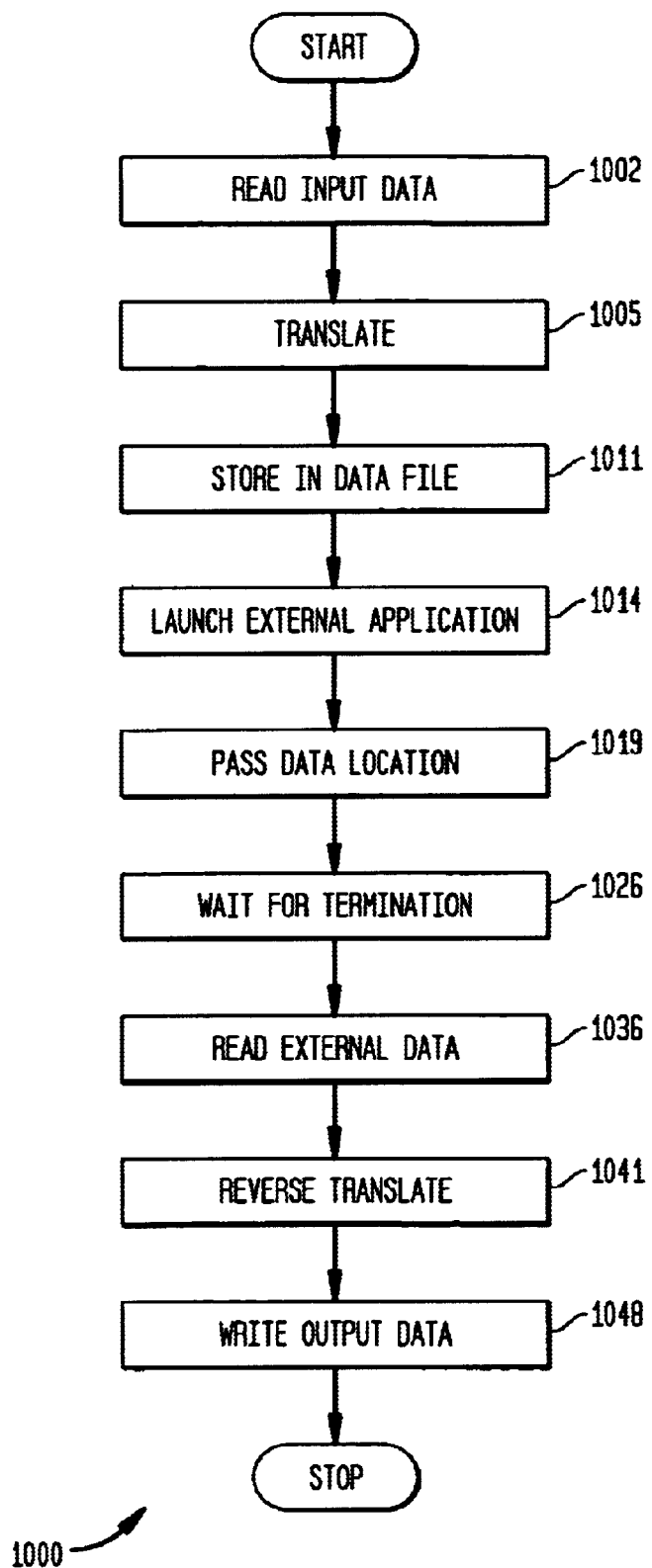

WORKFLOW CONFIGURATION AND EXECUTION IN MEDICAL IMAGING

BACKGROUND OF THE INVENTION

1. Field of the Invention

The present invention relates generally to medical imaging, and more particularly to workflow configuration and execution in medical imaging.

2. Description of the Background Art

Medical imaging is one of the most useful diagnostic tools available in modern medicine. Medical imaging allows medical personnel to non-intrusively look into a living body in order to detect and assess many types of injuries, diseases, conditions, etc. Medical imaging allows doctors and technicians to more easily and correctly make a diagnosis, decide on a treatment, prescribe medication, perform surgery or other treatments, etc.

There are medical imaging processes of many types and for many different purposes, situations, or uses. They commonly share the ability to create an image of a bodily region of a patient, and can do so non-invasively. Examples of some common medical imaging types are nuclear imaging, magnetic resonance imaging (MRI), ultrasound, X-rays, tomography of various types, etc. Using these or other imaging types and associated machines, an image or series of images may be captured. Other devices may then be used to process the image in some fashion. Finally, a doctor or technician may read the image in order to provide a diagnosis.

The image may capture various details of the subject, which may include bones, organs, tissues, ducts, blood vessels, nerves, previous surgical artifacts such as implants or scar tissue, etc. The image or images may be two-dimensional (i.e. planar) or three-dimensional. In addition, the image capture may produce an image sequence or video that shows live operation, such as a functioning organ, for example. An imaging machine may capture an image, manipulate it, process it in some fashion in order to improve the image, display it to a doctor or technician, and store it for later use.

Computerized image processing generally requires that the image data conform to some sort of protocol, with the protocol being a set of rules and standards that ensure that the information may be efficiently communicated and manipulated among different apparatus. The Digital Imaging and Communications in Medicine (DICOM) standard provides a well-defined and accepted data format and interaction protocol for communicating a processing medical image data, and is incorporated herein by reference. The DICOM standard is available from the Radiological Society of North America, Oak Brook, Ill. 60523-2251.

The DICOM standard has become popular for medical imaging because it ensures that conforming machines can operate on image data communicated from other conforming machines. Machines that may employ the DICOM standard may be workstations, CT scanners, MR images, film digitizers, shared archives (storage devices), printers, and other devices that may be used to process and store image and patient data.

FIG. 1 shows a typical medical imaging system 100. The medical imaging system 100 may include an imager 107 and imager controller 106 (they may be an integrated device), a patient database 110, an output device 115, a scanner 117, and one or more workstations 122. The imager 107 and imager controller 106 capture an image or images of a patient. The imager 107 may be, for example, a gamma ray camera, an X-ray imager, a magnetic resonance imager (MRI), an ultrasound imager, etc. The patient database 110 may store patient information (i.e., a plurality of records containing a name, vital parameters, a doctor, medical conditions, etc.), and imaging data. The output device 115 may be, for example, a printer, a computer monitor or other display screen, a film developer, etc. The scanner 117 may be a scanning device that digitizes an image. The workstations 122 may be used to access the patient database 110 in order to add or retrieve data. The various components may be connected by a distributed electronic network 103, such as, for example, a local area network (LAN), a wide area network (WAN), a virtual private network (VPN), or the Internet. The individual components may therefore be located in separate rooms, floors, buildings, or even separate hospitals or clinics.

Medical imaging in the prior art suffers from drawbacks in the piecemeal fashion in which the imaging process is handled. The prior art medical imaging typically handles the imaging process in independent segments. Multiple machines or computers are employed, with each machine or computer performing a portion of the overall imaging process. This requires more human oversight in order to configure and control multiple independent operations.

In the prior art, a technician may need to access and operate multiple machines in order to access patient data, enter patient data, configure a scan, perform image processing on a resulting scan, and store and retrieve the image data and patient data.

The prior art does not necessarily re-perform subsequent processing steps if a prior processing step or parameter is changed; therefore image accuracy may be compromised.

The prior art does not give an operator overall control over an imaging machine and processing. The operator therefore does not have cohesive control of a medical imaging process. The prior art further does not allow an operator to compose one overall processing schedule.

Improvements in workflow configuration and execution in medical imaging are needed to address these shortcomings in the prior art.

SUMMARY OF THE INVENTION

A first computer-implemented method of workflow configuration and execution in medical imaging is provided according to the invention. The method comprises the steps of creating and storing a workflow template (the workflow template comprises a standard form for entering data and activities), creating an imaging workflow routine by filling out the workflow template with data and a sequence of activities, and executing the sequence of activities according to the workflow template.

A second computer-implemented method of workflow configuration and execution in medical imaging is provided according to the invention. The method comprises the steps of configuring an image capturing sequence as part of a workflow template and configuring an image processing sequence as part of the workflow template. The method further comprises the steps of controlling execution of the image capturing sequence and the image processing sequence using the controller, with the controller executing the steps of the workflow template. The method further comprises the steps of detecting any change made to the workflow template and re-executing an affected, already executed portion of the workflow template if the workflow template has been modified.

A third computer-implemented method of workflow configuration and execution in medical imaging is provided according to the invention. The method comprises the steps of recalling an empty workflow template, adding patient data to the workflow template, and creating a sequence of activities in the workflow template. The workflow template thereby controls a medical imaging process when executed.

A workflow manager apparatus for workflow configuration and execution in medical imaging is provided according to the invention. The workflow manager apparatus includes at least one I/O device capable of being used by an operator to communicate with the apparatus. The workflow manager apparatus further includes a network interface capable of communicating over a distributed electronic network. The workflow manager apparatus further includes a memory capable of storing a workflow template and a DICOM medical imaging protocol. The workflow manager apparatus further includes a CPU that communicates with the I/O device, the network interface, and the memory. The CPU is capable of creating and storing a workflow template, filling out the workflow template with data and a sequence of activities in response to inputs from the I/O device, and executing the sequence of activities according to the workflow template.

The above and other features and advantages of the present invention will be further understood from the following description of the preferred embodiments thereof, taken in conjunction with the accompanying drawings.

BRIEF DESCRIPTION OF THE DRAWINGS

FIG. 10 is a flowchart of an external application interface method.

DETAILED DESCRIPTION OF THE PREFERRED EMBODIMENTS

Figure 1:
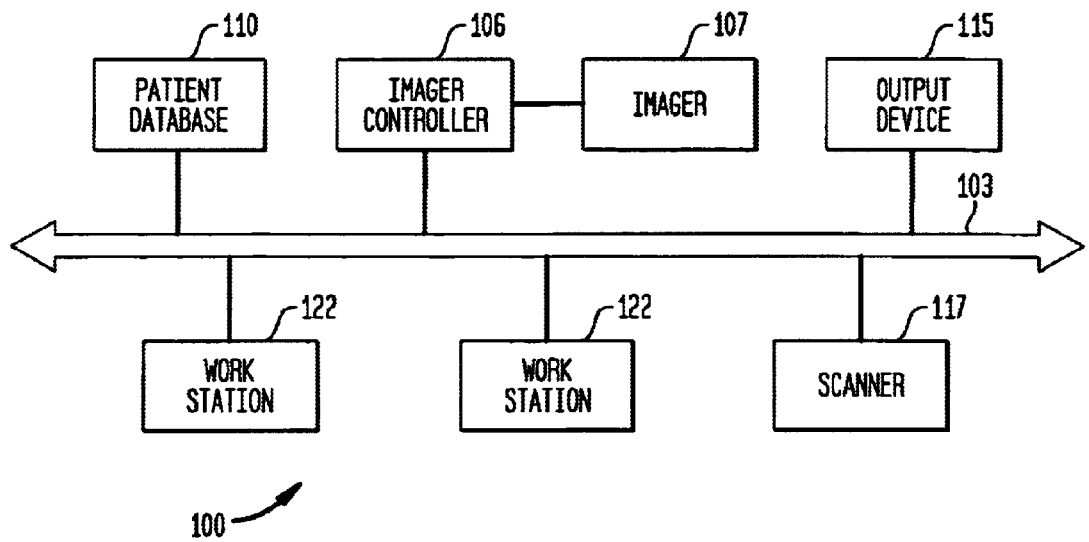
FIG. 1 shows a typical medical imaging system.
Figure 2:
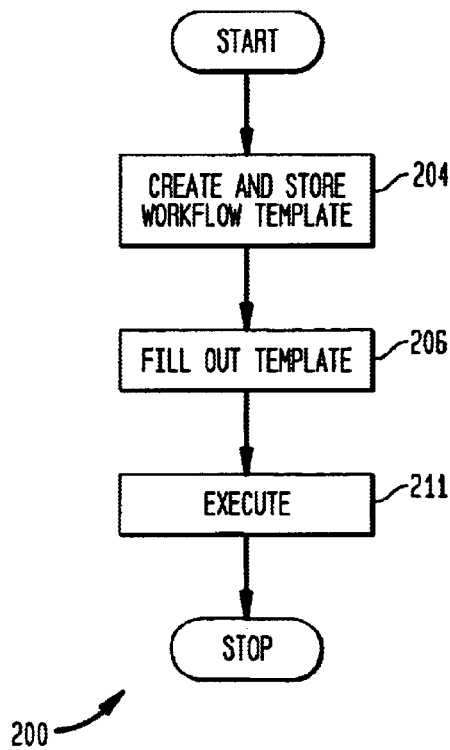
FIG. 2 shows a flow chart of initiating workflow execution according to the present invention.

FIG. 2 shows a flow chart 200 of workflow execution initiation according to the present invention. The method may be implemented by computer software running on a workflow manager apparatus. The workflow manager apparatus communicates with various devices in a medical imaging system, including imagers, workstations, input and output devices, etc. The computer software may be running on any imaging system device that is capable of communicating with other imaging system devices and capable of controlling the other devices.

In step 204, a workflow template is created and stored by a user. The workflow template produced in this step is a blank template that may be used to perform a particular process, and generally contains no patient data, but rather processes to be performed on patient data. The workflow template is thus a set of linked activities and activity properties that specify a workflow, while the workflow is a workflow template combined or associated with patient data, i.e., that can be executing, suspended, or ready for completion.

The workflow template defines a set of interconnected activities and their properties (an activity is a typical unit of work performed in the medical imaging process). A sequence of activities can therefore be used to perform an entire medical imaging task. For example, an activity can include acquiring patient data, organizing patient data, acquiring an image such as a nuclear or MRI image, processing the image through filtering or other image improvement methods, and outputting image data or other patient data.

Activities can have a variable number of inputs and outputs. However, in most cases, the number of inputs and outputs of an activity are fixed. A workflow activity has connectors that can be linked to connectors of other activities in order to exchange data. An input connector is used to input data from other activities and an output connector is used to provide data for other activities. An input connector of an activity is only allowed to connect to an output connector of a previous activity in the workflow sequence. Each output connector has a data type associated with it, and therefore an input connector is only allowed to connect to an output connector with a compatible data type. (Note, this does not necessarily mean one of identical type). In addition to input and output connectors, an activity may contain one or more print areas which contain data processing results for display by print area display objects.

Note that an activity may be contained in a workflow multiple times if necessary. For example, if a workflow requires two identical acquisitions to be performed, the activity implementing the acquisition could be included in the workflow twice.

A workflow template stores the definition of a workflow so that it can be executed later. This allows the same sequence of steps to be applied to multiple patients, implementing a fixed diagnostic protocol. The following information is contained in a workflow template. First, an ordered list of activities is constructed in the workflow template. Each activity has parameters and the activities connection stored with it. Second, the workflow template includes any actions to be taken when the operator completes the workflow. Third, the workflow template includes the activity that is expanded when the template is initially launched. An expanded activity is an activity that is shown in greater detail in a patient display or on an output device such as a computer monitor, for example. Expanded activities are discussed in conjunction with FIG. 9 below.

Workflow templates may be identified by a name, a category, an icon, and a descriptive phrase. The descriptive phrase displayed in the workflow browser more fully describes the workflow template. The icon gives a visual indication of the purpose or category of the particular workflow template. A category refers to a type of activity, such as an MRI scan activity, for example. The categories are used to group workflow templates in the workflow browser. The operator may define new categories and assign workflow templates to those categories. When the operator selects a workflow template, the operator is able to either view all workflow templates or view only those in a specific category.

An operator can make a new workflow template from an existing workflow template by adding or removing activities and/or modifying the properties of one or more activities and saving the modified workflow template file as a new file. Workflow templates stored on one system on a network can be launched by other machines on the network. This allows the same clinical protocol to be used in all systems on the network.

In step 206, the workflow template is filled out by adding applicable patient data. The activities contained within the workflow template may optionally be changed also. The workflow template may be a previously stored template or a newly created template.

The patient data may be obtained from the patient database 110, from a hospital information system (HIS), a radiological information system (RIS), or may be manually entered by the operator. The patient data from the patient database 110 can be automatically passed to a Data Selection activity (typically the first activity in the sequence of activities of the workflow template) or may be interactively selected by the user from the patient database 110.

Preferably, the patient data is arranged in the patient database 110 in a manner consistent with the DICOM standard (i.e., by patient, study, series, and image). A patient browser may allow the operator to interactively view the patient database 110, and preferably allows the operator to view the patient database 110 at different levels of detail. For example, the patient browser may allow the operator to examine the patient database 110 on a patient level. At the patient level, each patient in the patient database 110 can be viewed. The details of the studies and the image series for a patient may not be viewable at this level. At a study level, each study for each patient may be viewed independently. The details of the series for each patient may not be viewable at this level. At a series level, each series for each patient may be viewed independently.

In step 211, the workflow template is executed to perform the workflow of the medical imaging procedure. The execution generally proceeds in a conventional sequential fashion. In one embodiment, execution is controlled by a processing token that is passed to a currently executing activity of the sequence of activities. The sequence of activities may include external applications, and therefore the processing token may be passed to an external application interface that communicates with the external application and transfers data and controls execution of the external application.

Execution of the completed workflow template is generally continuous, but may be paused by the operator. In addition, the execution may be reset to a previous activity and re-started if a workflow parameter has changed. In one embodiment, any such change is automatically detected and the execution of the workflow is automatically reset to a workflow template position and activity that will re-process the changes. Alternatively, a re-execution of affected activities may only be initiated upon a command or input by an operator or technician.

A workflow can be in various states, such as pending, running, suspended, or ready for completion. In the pending workflow state, the workflow has not yet been run and is stored and is ready for execution. In a running workflow state, the workflow is loaded into system memory of a computer system and is actively acquiring or processing patient data. In the paused workflow state, the workflow is loaded into memory, but is not active. Only in the paused workflow state can the structure of the workflow be modified. In the suspended workflow state, the partially run workflow is not resident in memory but is stored with its partial results. It can be reset to the running state by the operator. Upon being reset to the running state, the partial data will be restored and workflow will resume executing at the point where it was suspended. In the ready for completion workflow state, all activities and workflow have finished processing.

A workflow can perform a number of actions during completion of processing. It can save the contents of any output connector to the patient database 110 or other archive device. It can print all specified hard copies. It can send the workflow results to another system via the distributed electronic network 103. It can also make the information available for web viewing. Finally, it can create another workflow in the pending state with the results of the current workflow as the new workflow's input data. The presence and state of a workflow can be shown on all systems connected to the system on which the work is executing.

Furthermore, a pending or suspending workflow on one system can be launched on any other system on the network.

At any time, only one activity in the workflow is active. This activity is said to have the processing token. When a workflow is launched and begins execution, the first activity contained in the workflow is given the processing token and begins execution. Once this activity finishes, the processing token is passed to the next activity, and so on. Each activity in a running workflow exists in one of three states—ready, executing or finished. In the ready state, the activity needs to get the processing token. Either the processing token has not yet reached the activity, the activity was paused before finishing its task, or the operator has performed some action that requires the activity to be reprocessed. In the executing state, the activity has the processing token and is waiting for operator input or is actively acquiring or processing patient data. In the finished state, the activity has finished its task. For example, a data acquisition is complete or the workflow processing is complete.

The operator is allowed to change parameters and activities during execution of a workflow. When the activity that has been changed during execution has finished processing, the processing token will be reset to the changed activity. Subsequently, the processing may resume at the changed activity and move sequentially through the succeeding activities until all activities have finished processing the updated parameters.

Figure 3:
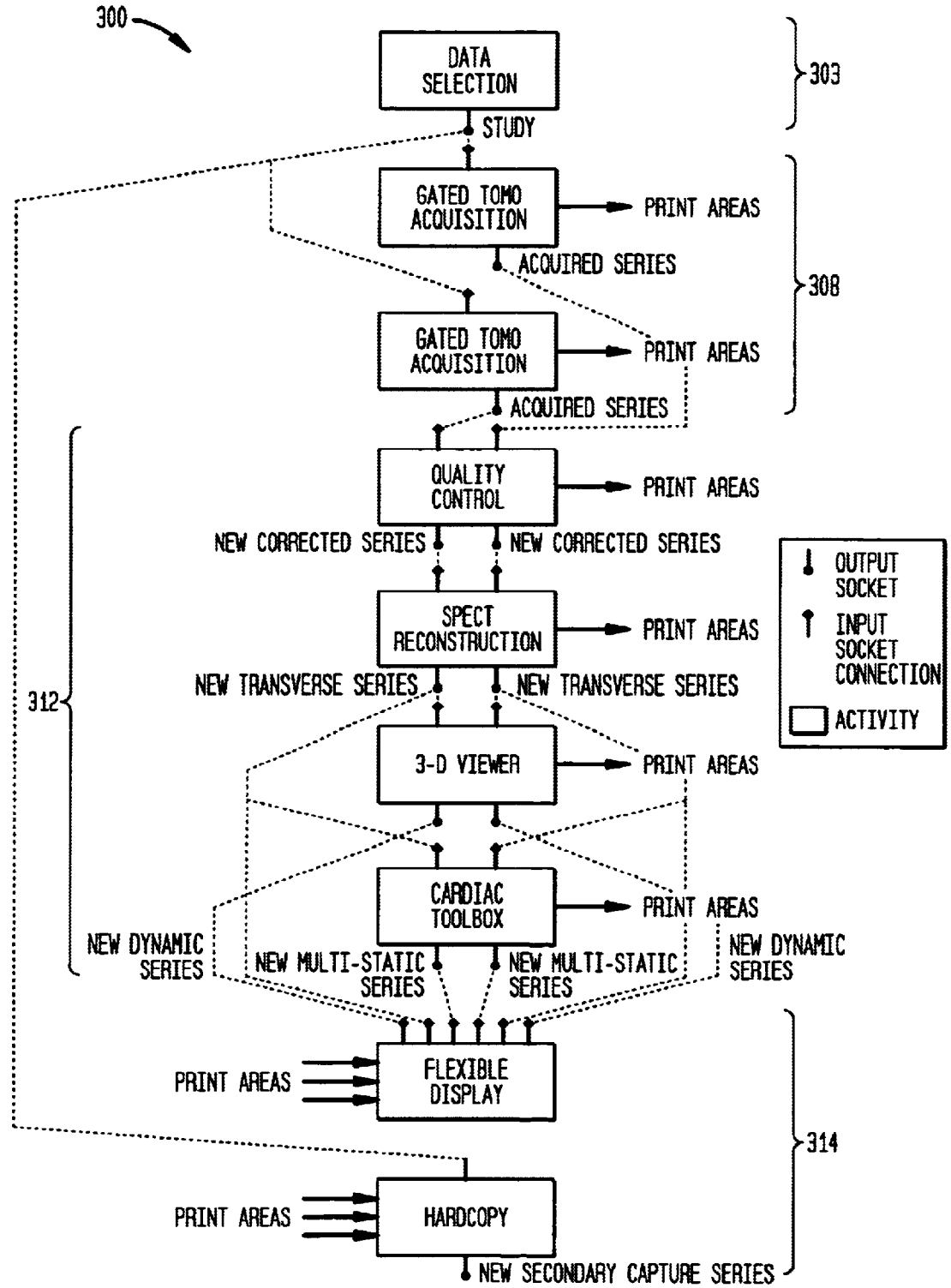
FIG. 3 shows a representative example of a workflow process.

FIG. 3 shows a representative example of a workflow process 300. In area 303, data selection is performed. This may include gathering patient data from the patient database 110, for example.

In area 308, image acquisition is performed. This may include any type of medical imaging process, such as MRI imaging, x-rays, ultrasound, tomography, nuclear (i.e. gamma ray) imaging, etc.

In area 312, the image is processed in some manner. The processing may include various types of filtering and image improvement algorithms. For example, a single photon emission computer tomography (SPECT) reconstruction may be used in order to obtain a suitable image or images, including three-dimensional images and real-time images of a bodily region or organ of interest.

However, SPECT scans are not normally readable and useful without intensive computer processing in order to create and refine the resulting image. The photons emitted during a SPECT scan may be scattered during passage out of the patient. Non-detection of photons scattered away from the detection apparatus and detection of photons scattered into the detection apparatus result in image degradation. Acquiring and processing a SPECT image therefore must involve compensating for and adjusting many physical and system parameters. The physical and system parameters may include attenuation, scatter, uniformity and linearity of detector response, geometric spatial resolution and sensitivity of the collimator, intrinsic spatial resolution and sensitivity of a detection apparatus, energy resolution of the electronics, system sensitivity, image truncation, mechanical shift of the camera or camera support structure, electronic shift, axis-of-rotation calibration, image noise, image slice thickness, reconstruction matrix size and filter, angular and linear sampling intervals, statistical variations in detected counts, changes in field of view with distance from the source, and system deadtime. Calibrating and monitoring many of these parameters fall under the general heading of quality control.

Various other types of tools may be used for imaging various bodily organs, such as a cardiac imaging software application. One such software is the Emory Cardiac Toolbox™, which is commercially available. The Emory Cardiac Toolbox™ facilitates readings of cardiac positron emission tomography (PET) and SPECT scans into an integrated software system. The Emory Cardiac Toolbox™ may be used to quickly and efficiently evaluate cardiac perfusion and function.

In area 314, the image and data results may be output in some manner for use by a physician or technician. This may include paper printouts, screen displays, generated film or negatives, etc. The output function may include a Flexible Display activity that provides a mechanism for a operator to customize the display. The Flexible Display activity allows the operator to configure and position an arbitrary number of display objects on an output screen (a display object is used to display information to the operator). A display object may be a screen area that can be changed in size and position. There may be a number of display object types, with each type being designed to display different types of information. An Image Display object may display a single image at a time, or display a movie or slideshow of a series of images. A Series Display object may display a group of images arranged in a raster fashion. A Slice Display object may display orthogonal slices of a region of interest, with the slices being aligned along the 3 axes of a volume. A Curve Display object may display a graph of a one or two dimensional vector of data. A Text Display object may display arbitrary text, textual patient data (such as a patient name, for example), or other text annotation from a study. A Bitmap Display object may display a non-diagnostic image or graphic (such as an institution's logo, for example). The Print Area Display object may display a print area from a previous activity in the workflow. This allows output from other activities to be incorporated into a display page.

The Flexible Display activity allows an operator to create multiple display pages, and each page may be separately configured. The Flexible Display activity may include page layout and display modes. The Page Layout mode may be used to configure the information to be displayed on a page. In this mode, the display objects may be positioned and sized, and the individual properties of each display object can be set. Each display object will have zero or more input connectors. The Display mode is the normal mode of operation, and in this mode a display objects may not be positioned or sized. For example, in the Display mode, the operator can adjust a display contrast, run movies or series of images, etc.

Figure 4:
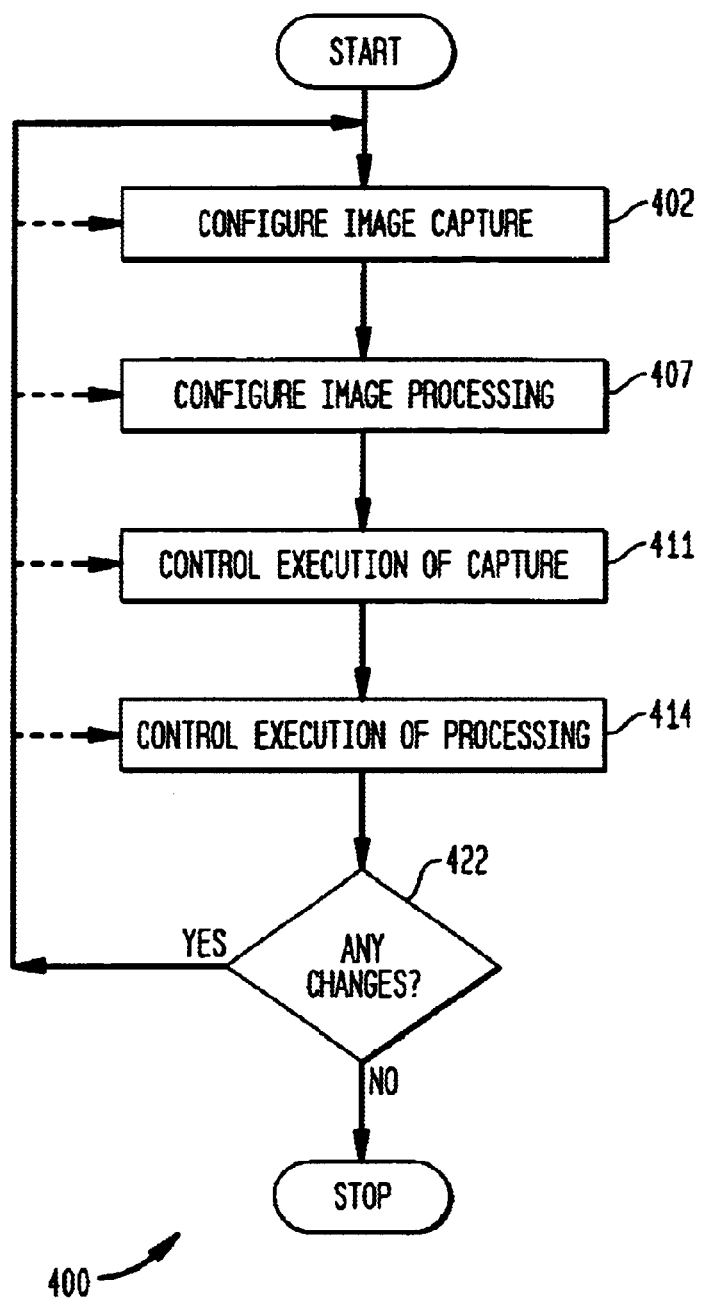
FIG. 4 is a flow chart image capture and process control.

FIG. 4 is a flow chart 400 of a process of controlling image capture and processing according to the invention. In step 402, the image capturing is configured. This may include selecting or configuring any variables needed to capture an image, including selecting an image capture type, an image capturing machine, etc.

In step 407, the image processing is configured. This may include selecting and configuring any type of post image-capture processing, including image combination, image manipulation, filtering, etc. Therefore, the image processing configuration may include specifying software packages or modules or specifying external applications that may be used in some manner to process the captured image or images.

In step 411, the workflow manager controls the execution of the image capture. This may include operating an imaging device according to workflow template instructions in order to capture an image or series of images.

In step 414, the workflow manager controls the execution of processing according to workflow template instructions. This may include passing a processing token between workflow activities, including external processing applications, may include starting and stopping applications, passing parameters, checking for completion of the image processing applications, etc.

In step 422, the workflow manager determines whether any changes have been made during processing. For example, if an operator or technician makes any changes to the workflow sequence, the method detects such a change and determines whether any reprocessing needs to be performed. Any affected, already executed activities may then be re-executed in order to ensure that the workflow is processed according to the instructions of the operator or technician. In this regard, it is noted that only activities that have been changed will be re-executed, as shown by the dashed arrows in FIG. 4. For instance, a change in a capture activity will re-execute the capture activity and the processing related to that capture activity, but not necessarily all processing. Similarly, a change to a processing activity will cause a re-execution of the processing activity and all subsequent activities depending on results of the changed processing activity, but will not re-execute capture activities.

Figure 5:
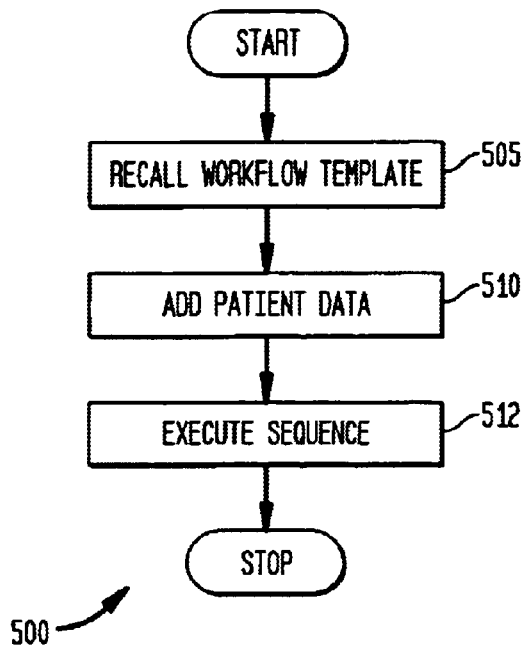
FIG. 5 is a flow chart of an alternate embodiment of FIG. 2.

FIG. 5 is a flow chart 500 of an alternative embodiment to FIG. 2. In step 505, an operator recalls a workflow template. Preferably, in medical imaging settings, multiple blank workflow templates (containing sequences of activities for certain tasks but no patient data) may already exist and be configured to perform specific tasks. For example, an operator or technician desiring to perform a gated tomography study of a particular bodily region or organ may look for a gated tomography workflow template containing desired imaging and processing steps. In this manner, the operator is saved from having to create an appropriate workflow template whenever processing needs to be done.

In step 510, the operator adds patient data into the selected workflow template. For example, the operator or technician may need to enter a patient name. In addition, some of the patient data may be obtained from the patient database 110 or HIS/RIS.

In step 512, the operator may initiate and control execution of the workflow (as specified in the workflow template). In addition, the operator may modify the existing workflow sequence of activities. This may occur before the workflow template is executed or may occur during execution or suspension of execution of the workflow template. For example, if the operator judges that the image resolution or quality is not acceptable, the operator may try different image processing techniques in order to achieve a desired quality in the finished image.

Figure 6:
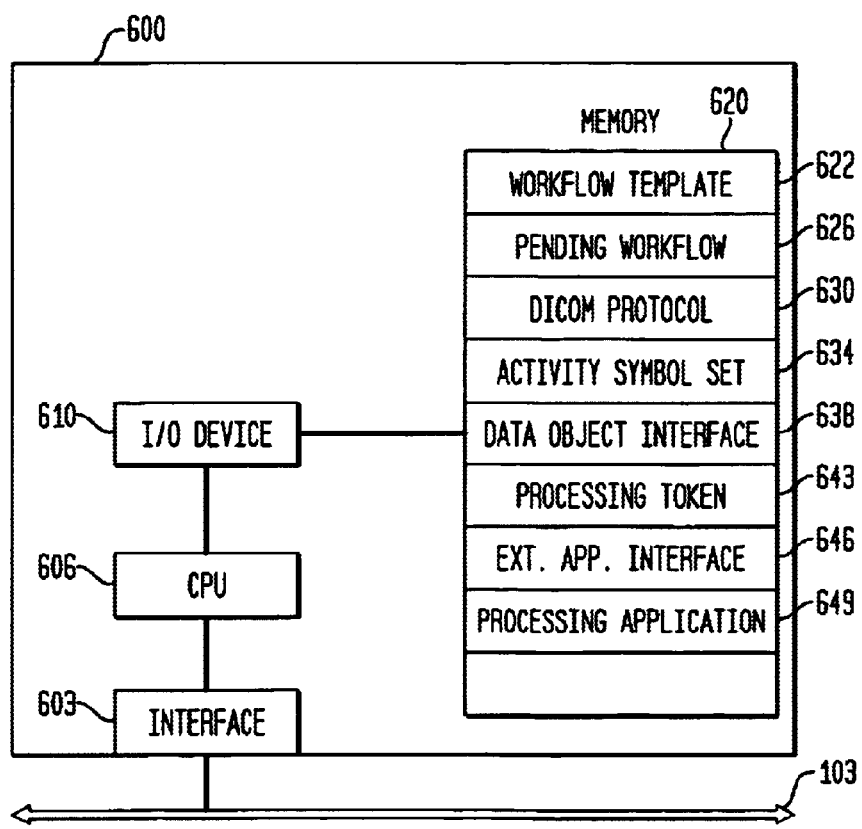
FIG. 6 shows a workflow manager apparatus for workflow configuration and execution in medical imaging.

FIG. 6 shows a workflow manager apparatus that may be used to control a workflow in a medical imaging process. The apparatus 600 may include a network interface 603, a CPU 606, at least one I/O (input/output) device 610, and a memory 620.

The workflow manager apparatus 600 may be connected to a distributed electronic network 103, such as a LAN, WAN, VPN, the Internet, etc., by the interface 603. The interface 603 may be any type of distributed electronic network interface, such as for example, a network card, modem, hub, router, gateway, etc.

The CPU 606 may be any type of general purpose CPU or processor used to run and control a computer or computer device.

The I/O device 610 may include any type of input device, such as, for example, a keyboard or keypad, a touch screen, a pointing device such as a joystick or mouse, etc. In addition, the at least one I/O device 610 can include any type of output, such as a computer monitor or display, a touch screen, a printer, a film developer, etc.

The memory 620 may be any type of digital memory, such as for example, random access memory (RAM), read-only memory (ROM), magnetic disk tape, bubble memory, optical memory, etc. The memory 620 stores data and executable instructions that may be used to operate the workflow manager apparatus 600. This may include an operating system and a workflow manager program.

The memory 620 may include at least one workflow template storage area 626, at least one pending workflow storage area 629, at least one DICOM protocol storage area 631, at least one activity symbol set storage area 634, at least one data object interface storage area 638, at least one processing token storage area 643, at least one external application interface storage area 646, and at least one processing application storage area 649.

The blank template storage area 626 may store one or more previously created blank workflow templates that include a sequence of activities, but do not include patient data.

The pending workflow storage area 629 may store one or more pending workflows that may be ready for execution. The pending workflows may include sequences of activities and all patient data needed to execute the activity. A pending workflow may alternatively include enough patient data for the workflow manager to access the patient data from the patient database 110.

The DICOM protocol area 631 may store any required DICOM protocol data, including rules for decoding and encoding DICOM message data.

The activity symbol set storage area 634 stores any symbols or icons created or used to denote a particular activity on a user's display screen. For example, a Butterworth filter activity may have a unique symbol or icon associated with it. Therefore, an activity symbol may represent a predetermined activity that performs a predetermined processing activity upon selection and execution.

The data object interface storage area 638 stores a data object interface 703 used to pass data between activities and between activities and system nodes, such as workstations, for example (see discussion below accompanying FIG. 7).

The processing token storage area 643 may store one or more processing tokens, such as a symbol or address, each indicating the application that currently is executing (or the application that may be allowed to execute if the operation is suspended).

As there is one token per workflow, multiple workflows can be run simultaneously by specifying multiple tokens.

The external application interface storage area 646 may store at least one external application interface created by a workflow template to allow communication between the workflow manager apparatus 600 and an external application. The external application may exist on the same computer as the workflow manager, or may exist on a physically separate or remote computer device connected to the distributed electronic network 103. For example, another workstation may possess a software application used for image or data processing, and that external application may be linked into a workflow template in order to perform a desired operation. Because of the non-integrated or remote nature of the external application, an external application interface must be created and stored in order to translate data between the apparatus 600 and the external application. In addition, the external application interface may control execution of the external application. The external application therefore must have data sent to it, must be told what to do, must be started, and must receive the data from the external application when it completes and terminates.

The processing application storage area 649 may store one or more external applications used to process the patient data or the image data. For example, the processing application storage area 649 may store a cardiac image processing software program, image filtering or processing software, viewing software, SPECT reconstruction software, etc.

Figure 7:
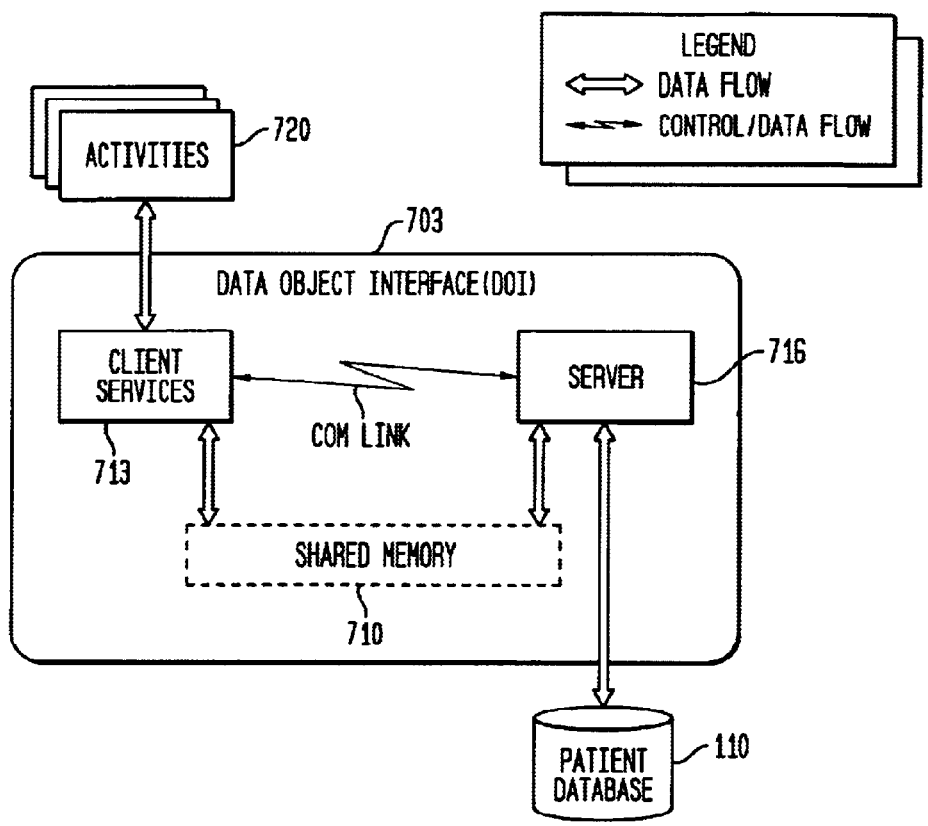
FIG. 7 shows a data object interface.

FIG. 7 shows a data object interface (DOI) 703 according to one embodiment of the invention. The DOI 703 includes a shared memory 710, a client services library 713, and a patient database server 716. The DOI 703 is a systems interface to the patient database 110 and provides access to the data stored in the patient database 110 via DOI objects. The DOI objects encapsulate the information stored in the patient database 110 and allow a workflow to read and write the information therein.

Activities are able to use the functionality provided by the DOI 703 by calling functions in the DOI client services library 713. The DOI 703 may also be used to communicate data between activities in the workflow by passing data between input and output connectors. The activity generating the data stores the data from its output connector in the DOI 703. A subsequent activity input connector may retrieve the data from the DOI 703.

Data and control information can be passed between the activity (using the client services library 713) and the DOI server 716 using, for example, Microsoft component object module (COM) calls. The DOI 703 determines whether the data is passed via COM calls or the shared memory 710. This choice is transparent to the operator.

For example, in order to fill patient data into an active workflow, the activity 720 requests the data from the client services library 713, which passes the request to the patient database server 716. The patient database server 716 retrieves the requested data from the patient database 110 and places it in the shared memory 710. The patient database server 716 signals to the client services library 713 that the data is ready, and the client services library 713 retrieves the data from the shared memory 710 and passes it to the requesting activity 720.

Other services the DOI may provide to the individual activities 720 may include creating a new instance of a DOI object, deleting an instance of a DOI object, getting or setting an attribute of a DOI object, saving an existing DOI object, saving a new database object, or creating a DOI object based on identifiers specifying an object in the database.

Figure 8:
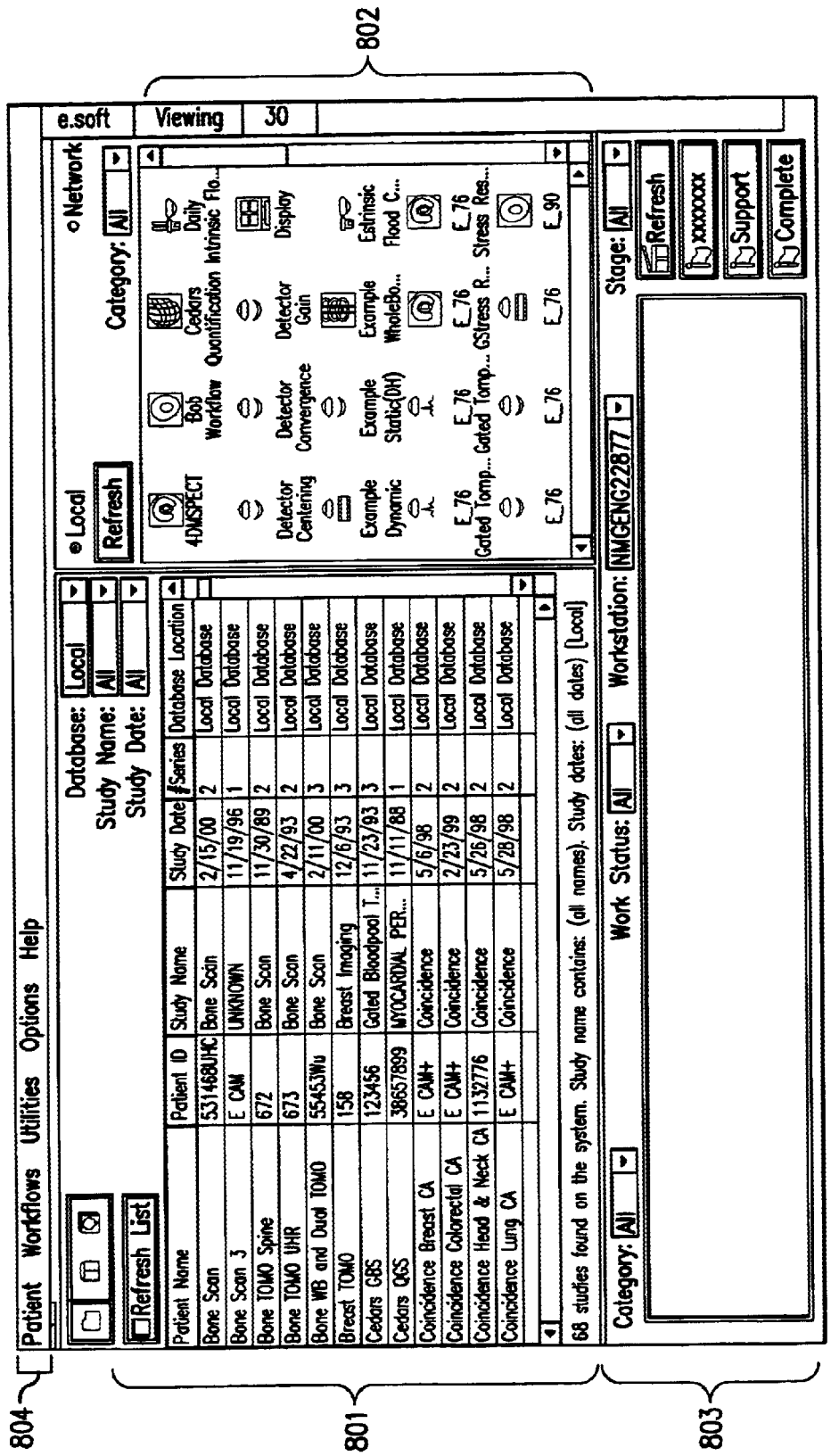
FIG. 8 shows a screen shot of a representative command module.

FIG. 8 shows a screen shot of a representative Command Module according to one embodiment of the invention. The Command Module is a graphical user interface (GUI) that allows an operator to create and/or configure a workflow template. In this embodiment, area 801 is a patient browser, area 802 is the workflow template browser, area 803 is a workflow manager access area, and area 804 is a menu bar.

Area 801, the patient browser, allows the operator to view individual patient data in the patient database 110 and to select patient data to include in a workflow template. In one embodiment of the command module, double clicking on patient data in the patient browser launches a workflow that is configured to display the selected data.

Area 802, the workflow template browser, allows the operator to interactively view all workflow templates or only workflow templates of a particular category. In one embodiment of the command module, double clicking a workflow template in the workflow template browser launches a new workflow, using the selected workflow template and the patient data currently selected in the patient browser.

Area 803, the workflow manager access area, allows the operator to view and control work flows. The workflow manager is updated whenever a operator launches a workflow from the command module.

Area 804, the menu bar, may contain menus of options for the operator. The patient menu may contain commands to work with patient data. The workflow menu may contain commands to launch and pause work flows. The utilities menu may contain commands to launch programs to configure the command software and to examine the printer queues. The options menu may give service options.

The help menu may provide help with usage or may connect a operator with an on-line help function.

Figure 9:
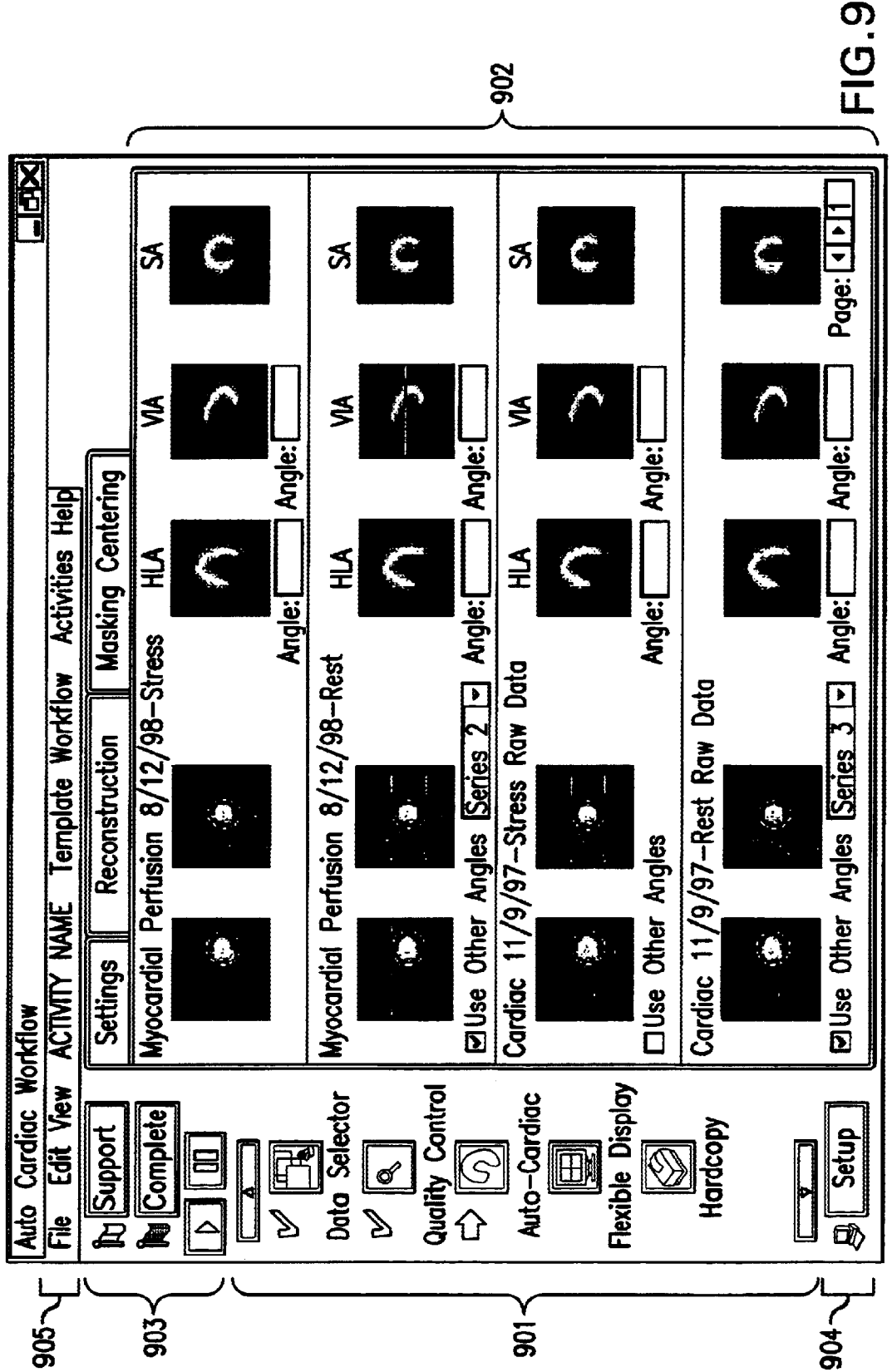
FIG. 9 shows a screen shot of a representative working screen.

FIG. 9 shows a screen shot of a representative operational workflow display according to one embodiment of the invention. The representative display is a GUI that allows an operator to access and to control an executing workflow template.

In area 901, the activities of the workflow in their current states are shown. The first activity in the workflow is shown at the top of area 901 and succeeding activities are shown in descending order. The right column shows the names and icons of the activities in the workflow, with each type of activity having its own unique icon and name. The left column shows the status of each of the activities as described above. Note that these columns may be scrolled up or down if there are too many activities in the workflow to be shown at one time. A status icon may be present in the display for each activity in the workflow. The status icon is used to indicate the state of the activity to the operator. In the current system, the ready state is a blank, the executing state is a (yellow) arrow, the pause state is a stop sign, and the finished state is a (green) checkmark. In the example shown, the first two activities have been completed, the third activity is executing, and the fourth and fifth activities are ready to execute.

Area 902 may contain an "expanded activity" (expanded to graphically show some or all images being captured or processed by the executing activity). The operator is able to control an expanded activity by clicking on the icon representing the activity in the workflow section of the system's GUI. An operator may expand and examine an activity without affecting the processing sequence. While one activity is expanded in area 902, for example, other activities may be running in the background.

Area 903 contains icons that may be used to change the state of the workflow. The (green) arrow may be clicked to resume a paused workflow. The (red) bars may be clicked to pause a running workflow. Selecting the "suspend" button will cause the workflow to be suspended. Selecting the "complete" button will cause the workflow (in which all activities have finished processing) to be completed.

Area 904 may contain a set-up button. When the operator clicks on this button, a screen may be displayed that allows the operator to configure the actions the workflow will perform during completion.

Area 905 is the workflow menu bar. The menu items may configure and control a workflow template in a manner similar to selection of an icon in any of the other areas. Note that the menu items may change based on a currently expanded activity.

The various icons used by the workflow manager and by the Command Module may be perceptible activity icons that by their very nature communicate some information to an operator. For example, a perceptible activity icon may show a bodily region or organ to be imaged, or may give some indication or symbol of a processing to be performed on an existing image.

FIG. 10 is a flowchart of an external application interface process 1000. In step 1002, external application input data is read from at least one external application input connector. This input data is the data to be processed by the external application.

In step 1005, the data is translated into an external application data format, if needed. This optional translation allows many different external applications to interface with and be used by the workflow manager.

In step 1011, the external application input data is stored in an external application data file. The external application data file holds the data and may be accessed by the external application when the external application is executing.

In step 1014, the external application is launched. The external application executes, using the external application data file as input. The external application execution may be controlled by a processing token that is passed to the external application interface.

In step 1019, the location of the external application input data or data file is passed to the external application. This may be, for example, a beginning memory location of the input data and a size of the input data. In this manner, the external application can access the external application data and use the external application data for processing.

In step 1026, the workflow manager waits for the external application to complete processing and terminate. As part of the external application processing, the external application may transform or create data, and may create an external application output file.

In step 1036, the external application output file is read in order to access any data output by the external application.

In step 1041, the output data may be reverse-translated by the application interface if necessary. The reverse translation may restore a data format originally translated by the application interface. For example, if an external application does not implement or use the DICOM protocol, the patient data passed to it may need to be re-arranged or transformed in some manner.

In step 1048, the external application output data may be placed onto at least one external application output connector. In this manner, any data operated on or produced by the external application may be passed on to other activities in the workflow.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A computer-implemented method of executing a medical imaging procedure on a patient, comprising the steps of:

creating and storing a workflow template, said workflow template containing a specific desired sequence of predefined medical imaging activities representing a particular medical imaging procedure, wherein each of said predefined medical imaging activities has at least one input connector and at least one output connector, each of said input and output connectors being associated with a data type, wherein links aria created between input and output connectors of different medical imaging activities only where associated data types of such activities are compatible with each other, and only output connectors of preceding activities in said sequence are capable of being linked to input connectors of subsequent activities, wherein said links transfer data from an output connector of one activity to an input connector of a linked activity;

retrieving a stored workflow template defining a particular medical imaging procedure desired to be performed;

entering into said retrieved workflow template particular patient data for a patient on whom the medical imaging procedure is to be executed; and executing said desired sequence of activities by invoking said workflow template in conjunction with medical imaging acquisition and processing equipment.

2. The method of claim 1, wherein said sequence of activities comprise the steps of:

selecting data;

acquiring at least one image;

processing said at least one image; and providing a processed image output.

3. The method of claim 1, further comprising the steps of:

detecting a change in said medical imaging procedure during said executing step if an activity change occurs; and re-executing only activities in said sequence subsequent to the activity in which said activity change occurs upon detection of said change in said medical imaging procedure.

4. The method of claim 1, wherein an external application interface may be created in a workflow template, said external application interface allowing an external application to be executed as an activity.

5. The method of claim 1, wherein an external application interface may be created in a workflow template, said external application interface allowing an external application to be executed as an activity, with said external application interface performing the steps of:

reading external application input data from at least one input connector to said external application;

translating said external application input data into an external application format, if necessary;

storing said external application input data in an external application data file;

launching said external application;

passing a location of said external application input data to said external application;

waiting for said external application to terminate;

reading external application output data In an external application output file created by said external application;

reverse translating said external application output data into an internal data format, if necessary; and placing said external application output data onto at least one external application output connector.

6. The method of claim 1, wherein a stored workflow template is capable of being launched by any device in communication over a communication medium with a system containing said stored workflow template.

7. The method of claim 1, wherein if an already-executed activity of saint sequence of activities is modified or invalidated, execution reverts to said already-executed activity.

8. The method of claim 1, wherein an activity is represented by a computer-displayed icon.

9. The method of claim 8, wherein an activity is chosen for inclusion in said sequence of activities by selection of said computer-displayed icon.

10. The method of claim 1, wherein at least one of said predefined medical imaging activities has at least two output connectors, each being connectable to input connectors of different subsequent activities.

11. The method of claim 1, wherein at least one of said predefined medical imaging activities has at least two input connectors, each being connectable to output connectors of different preceding activities.

12. A computer-implemented method of executing a medical imaging procedure on a patient, comprising the steps of:

configuring an image capturing sequence as part of a workflow process containing a sequence of defined executable activities wherein each of said activities has at least one input connector and at least one output connector, each of said input and output connectors being associated with a data type, wherein links are created between input and output connectors of different activities only where associated data types of such activities are compatible with each other, wherein said workflow process is stored in a memory of a computer;

configuring an image processing sequence as part of said workflow process;

executing said image capturing sequence by executing said workflow process;

executing said image processing sequence by executing said workflow process;

detecting a modification of an activity in said sequence as a change in said stored workflow process in real time during execution of an executing instance of said workflow process; and re-executing only activities in said executing workflow process that are subsequent to said modified activity in said sequence, if said stored workflow process has been modified.

13. The method of claim 12, wherein execution of said workflow process comprises the steps of:

selecting data for use in said process;

acquiring at least one image;

processing said at least one image; and providing a processed image output.

14. The method of claim 13, wherein said data comprises patient data.

15. The method of claim 12, wherein said steps of configuring include the step of connecting an output connector of a first activity within said sequence to an input connector of a second activity that is subsequent to said first activity, wherein said connection between said input connector and said output connector defines a data transfer between said first activity and said second activity.

16. The method of claim 12, wherein said workflow process further includes an external application interface as an executable activity, said external application interface allowing an external application to be executed as an activity.

17. The method of claim 12, wherein a stored workflow process is capable of being launched by any device in communication over a communication medium with a system containing said stored workflow process.

18. A workflow manager apparatus for carrying out a medical imaging procedure on a patient, comprising:
- at least one I/O device, said at least one I/O device capable of being used by an operator to communicate with said apparatus;
- a network interface capable of communicating over a distributed communication network with a plurality of devices used in said medical imaging procedure;
- a memory capable of storing a workflow template including a sequence of executable activities related to said medical imaging procedure wherein each of said activities has at least one input connector and at least one output connector, each of said input and output connectors being associated with a data type, wherein links are created between input and output connectors of different activities only where associated data types of such activities are compatible with each other, and a DICOM medical imaging protocol; and
- a CPU communicating with said at least one I/O device, said network interface, and said memory, with said CPU creating and storing a workflow template, filling out said workflow template with patient data to create a workflow, and executing said sequence of activities according to said workflow in response to inputs from said at least one I/O device.

19. The apparatus of claim 18, wherein said memory further contains a data object interface for interfacing to a patient database.

20. The apparatus of claim 18, wherein said memory further contains an external application interface that allows a workflow to link to and execute an external application.

* * * * *